United States Patent [19]
Luly et al.

[11] Patent Number: 5,744,661
[45] Date of Patent: Apr. 28, 1998

[54] PURIFICATION OF 1, 1-DIFLUOROETHANE

[75] Inventors: Matthew Hermes Luly, Lancaster; Addison Miles Smith, Amherst; Kane David Cook, Eggertsville, all of N.Y.

[73] Assignee: AlliedSignal Inc., Morristown, N.J.

[21] Appl. No.: 729,702

[22] Filed: Oct. 7, 1996

[51] Int. Cl.$^6$ .................................................. C07C 17/38
[52] U.S. Cl. ............................................................. 570/177
[58] Field of Search ............................................. 570/177

[56] References Cited

U.S. PATENT DOCUMENTS

| | | | |
|---|---|---|---|
| 3,218,364 | 11/1965 | Kometani et al. | 570/177 |
| 3,873,629 | 3/1975 | Jones | 570/177 |
| 3,995,010 | 11/1976 | Smalley et al. | 423/240 |
| 5,396,001 | 3/1995 | Pennetreau | 570/179 |

FOREIGN PATENT DOCUMENTS

| | | |
|---|---|---|
| 832502 | 6/1961 | Canada . |
| 92100314.5 | 7/1993 | China . |

*Primary Examiner*—Paul F. Shaver
*Attorney, Agent, or Firm*—Colleen D. Szuch

[57] ABSTRACT

A method for removing unsaturated impurities from 1,1-difluoroethane by intimately contacting the impure 1,1-difluoroethane with sulfuric acid. This process is especially useful for removing one or more unsaturated halocarbons having two carbon atoms such as vinyl chloride, vinyl fluoride and blends thereof from the 1,1-difluoroethane.

22 Claims, No Drawings

5,744,661

PURIFICATION OF 1,1-DIFLUOROETHANE

BACKGROUND OF THE INVENTION

1. Field of the Invention

The present invention relates to a method for the separation and purification of 1,1-difluoroethane (HFC-152a) from a mixture of HFC-152a with at least one unsaturated halocarbon having two carbon atoms. The invention is particularly useful for separating HFC-152a from its mixture with a vinyl chloride and/or vinyl fluoride impurity.

2. Description of the Prior Art

It is known in the art that HFC-152a is a hydrofluorocarbon compound useful as a refrigerant, propellant, and material used for producing fluoroplastics. HFC-152a is particularly advantageous as a substitute for certain chlorofluorocarbons, particularly as a substitute for dichlorodifluoromethane (CFC-12). The latter is undesirable due to its high ozone depletion potential (ODP) while 1,1-difluoroethane has an ODP of zero and global warming potential (GWP) of just 0.02. HFC-152a can be prepared by reacting hydrogen fluoride with chlorocarbons such as vinyl chloride or dichloroethane, as described in Canadian Patent 832,502, which is incorporated herein by reference.

Most 1,1-difluoroethane production processes co-produce some undesirable unsaturated halocarbons such as vinyl fluoride monomer (VFM). If a chlorinated feed stock is used, vinyl chloride monomer (VCM) is also co-produced. Both of these unsaturated compounds have adverse health effects on humans and must be removed or reduced to extremely low levels. Although distillation is effective in removing most other impurities resulting from the production of 1,1-difluoroethane, vinyl chloride and vinyl fluoride are especially difficult to remove in this manner.

There have been various attempts in the art to purify 1,1-difluoroethane. U.S. Pat. No. 5,396,001 discloses purification of 1,1-difluoroethane using active carbon to absorb vinyl chloride. This method is disadvantageous because it has a very low capacity for absorbing vinyl chloride. It is also not effective for removing vinyl fluoride. Chinese Patent Application CN 1074434 discloses a process of photochlorination to remove vinyl chloride from 1,1-difluoroethane. The vinyl chloride is chlorinated to trichloroethane and other alkyl halides which can be separated from 1,1-difluoroethane. This method has the undesired effect of reacting some 1,1-difluoroethane to HFC-142b, which results in a yield loss. This latter method is also unable to achieve very low (ppm) levels of vinyl chloride. U.S. Pat. No. 3,995,010 discloses the removal of vinyl chloride from gaseous streams using an aqueous medium containing hypochlorous acid. However, this method is inefficient because it results in undesirable by-products and is also unable to achieve very low (ppm) levels of vinyl chloride.

Although 1,1-difluoroethane is a very useful compound which would benefit the environment greatly by replacing chlorofluorocarbons, the undesirable by-products formed in its production pose a risk to human health. It would be desirable to develop a method to significantly reduce the levels of unsaturated halocarbons such as vinyl chloride and vinyl fluoride resulting from 1,1-difluoroethane production.

It has now been found that sulfuric acid can be used to remove unsaturated halocarbon compounds such as vinyl chloride and vinyl fluoride from mixtures with 1,1-difluoroethane. Through intimate contact with 1,1-difluoroethane, sulfuric acid has been unexpectedly found to absorb and react with these unsaturated impurities, thereby removing them from the mixture.

SUMMARY OF THE INVENTION

The present invention provides a method of purifying 1,1-difluoroethane which comprises contacting a mixture comprising 1,1-difluoroethane and at least one unsaturated halocarbon having two carbon atoms, with sufficient sulfuric acid under conditions sufficient to separate 1,1-difluoroethane from the at least one unsaturated halocarbon having two carbon atoms.

This invention also provides a method of purifying 1,1-difluoroethane which comprises contacting a gaseous mixture comprising 1,1-difluoroethane and at least one unsaturated halocarbon having two carbon atoms with sufficient liquid sulfuric acid under conditions sufficient to separate 1,1-difluoroethane from the at least one unsaturated halocarbon having two carbon atoms.

This invention further provides a method of purifying 1,1-difluoroethane which comprises contacting a gaseous mixture comprising 1,1-difluoroethane and at least one unsaturated halocarbon having two carbon atoms, with liquid sulfuric acid by flowing the gaseous mixture through a vessel and flowing sufficient liquid sulfuric acid through the vessel countercurrent to the gaseous mixture to separate 1,1-difluoroethane from the at least one unsaturated halocarbon having two carbon atoms.

DETAILED DESCRIPTION OF THE PREFERRED EMBODIMENT

In the practice of the present invention, a method is provided which comprises contacting a mixture comprising HFC-152a and at least one unsaturated halocarbon having two carbon atoms, with sufficient sulfuric acid under conditions sufficient to separate HFC-152a from the at least one unsaturated halocarbon having two carbon atoms. In the preferred embodiment, the HFC-152a is separated from vinyl chloride, vinyl fluoride, or a blend of vinyl chloride and vinyl fluoride.

As used in the present invention, an unsaturated halocarbon having two carbon atoms is meant to encompass molecules having only carbon, halogen and optionally hydrogen atoms. The preferred halogens are chlorine and fluorine. Such may contain from one to four halogen atoms substituted onto the carbon atoms. Such include molecules having more than one different halogen atoms. The balance of the carbon substituents, if any, are hydrogen atoms. Examples, non-exclusively, include one halogen-containing compounds such as vinyl chloride and vinyl fluoride; two halogen-containing compounds such as vinylidene chloride and vinylidene fluoride; three halogen-containing compounds such as trichloroethylene and trifluoroethylene; as well as four halogen-containing compounds such as perchloroethylene and perfluoroethylene. Mixed halogen compounds non-exclusively include 1-chloro-1-fluoroethylene, among others.

In the preferred embodiment, the mixture of 1,1-difluoroethane with the at least one unsaturated halocarbon having two carbon atoms is in the form of a gas. In the preferred embodiment, the amount of the at least one unsaturated halocarbon having two carbon atoms ranges from about 0.1 parts per million (ppm) to about 10 weight percent based on the weight of the overall mixture prior to separation. A more preferred range is from about 1 ppm to about 5 weight % and most preferably from about 5 ppm to about 1 weight %. The mixture is contacted with an amount of sulfuric acid effective to separate 1,1-difluoroethane from the unsaturated halocarbon having two carbon atoms. In the preferred embodiment, the sulfuric acid is a liquid. The sulfuric acid is preferably present in a large excess. The reaction may be conducted at any convenient sulfuric acid contact time which may be easily determined by those skilled in the art. For purposes of this invention, contact time is defined as the total volume of sulfuric acid in a reactor divided by the volumetric flow rate of the reaction mixture of HFC-152a and unsaturated halocarbons contacting the sulfuric acid. For purposes on this invention, the term sulfuric acid includes fuming sulfuric acid or oleum. When the sulfuric acid is spent, it is simply replaced.

The reaction may be conducted at any convenient contact time such as from about 1 second to about 10,000 seconds, preferably from about 5 seconds to about 5,000 seconds, more preferably from about 50 seconds to about 1,300 seconds, and most preferably from about 10 seconds to about 1,000 seconds. Larger contact times are also economically possible and may be easily determined by those skilled in the art. For example, the mixture of HFC-152a and the unsaturates may be continuously fed at a desired rate through a vessel containing a large excess of concentrated (>90%) sulfuric acid.

In the preferred embodiment, after the removal reaction, the resultant separated 1,1-difluoroethane contains about 1 ppm or less of the vinyl chloride, vinyl fluoride, or a blend thereof. More preferably the resultant separated 1,1-difluoroethane contains about 0.5 ppm or less, and most preferably about 0.1 ppm or less of the at least one unsaturated halocarbon having two carbon atoms.

One preferred method of contacting the mixture with the sulfuric acid is to bubble the gaseous mixture through sufficient liquid sulfuric acid to thereby separate the 1,1-difluoroethane from the at least one unsaturated halocarbon having two carbon atoms. The reaction may be conducted at room temperature or any convenient temperature such as a temperature of from about 10° C. to about 338° C., more preferably from about 10° C. to about 55° C. Temperature is not critical and in the most preferred embodiment is conducted at about room temperature. The reaction may be conducted at atmospheric pressure or any convenient pressure such as a pressure of from about 1 psia to about 500 psia, more preferably from about 10 psia to about 30 psia. Pressure is not critical and in the most preferred embodiment is conducted at standard atmospheric pressure. The aforementioned mixture of HFC-152a and vinyl unsaturates may contact the sulfuric acid in any way known in the art, such as mixing or agitating in a vessel such as a scrubbing column.

Another preferred method non-exclusively includes contacting the gaseous mixture with liquid sulfuric acid by flowing the gaseous mixture through a vessel and flowing sufficient liquid sulfuric acid through the same vessel countercurrent to the gaseous mixture to thereby separate 1,1-difluoroethane from the unsaturated halocarbon. The gas containing the unsaturated halocarbon may be contacted with the sulfuric acid either batchwise, semi-continuously, or continuously and in the preferred embodiment is contacted by countercurrent or co-current absorption in a packed tower. Alternatively, the gas containing the HFC-152a and unsaturated halocarbon may be contacted by sparging the gas into a liquid medium, which is preferably static, containing the sulfuric acid. When a packed tower is employed, the gas containing the HFC-152a and unsaturated halocarbon may be introduced to the tower at a point below the liquid level in the tower.

The following non-limiting examples serve to illustrate the invention.

EXAMPLE 1

A 2 inch diameter glass column was fitted at the bottom with a sintered metal frit (60 micron). Enough 96 weight percent sulfuric acid was added to fill the column 3 feet (about 1,853 cc). A feed mixture of 1,1-difluoroethane containing 1019 ppm of VCM was bubbled through the column at a rate of 67 g/hr. The scrubbed gas leaving the top of the column was captured at the beginning, middle, and end of the experiment and found to contain 508, 399, and 295 ppm, respectively. The VCM concentration was therefore reduced by a factor of at least 2.

EXAMPLE 2

Example 1 was repeated, except using 1,1-difluoroethane feed containing 328 ppm VCM. The scrubbed gas contained 211, 178, and 149 ppm VCM when sampled at the beginning, middle, and end of the experiment.

EXAMPLE 3

Example 1 was repeated, except using a 2 micron frit and a 1,1-difluoroethane feed containing 920 ppm VCM. The feed rate was about 58 g/hr and the scrubbed 1,1-difluoroethane contained 16, 16, and 15 ppm VCM when sampled at the top of the column.

EXAMPLES 4–10

These examples were performed as in Example 1 except for the differences cited in the table below.

| EXAMPLE | Feed VCM Conc. (ppm) | Column Diameter (inch) | Feed Rate (g/hr) | Average Exit Stream VCM (ppm) |
|---|---|---|---|---|
| 4 | 76.4 | 2 | 58 | 2.9 |
| 5 | 1022 | 1 | 58 | 1.2 |
| 6 | 45000 | 2 | 58 | 805 |
| 7 | 11.2 | 2 | 58 | 2.0 |
| 8 | 13 | 2 | 58 | 0.8 |
| 9 | 8 | 2 | 346 | 2.4 |
| 10 | 8 | 2 | 15 | 1.1 |

EXAMPLE 11

Example 1 was repeated except using a 9/16" plastic column, 100 cc of 96 weight percent sulfuric acid, and a glass frit. The feed 1,1-difluoroethane contained 1% each of vinyl chloride and vinyl fluoride and was fed to the sulfuric acid at a rate of about 10 g/hr. At the end of the experiment the vinyl chloride was reduced to 10 ppm and the vinyl fluoride was less than 1 ppm.

EXAMPLE 12

A Teflon lined autoclave was charged with 100 ml of 96 weight percent sulfuric acid and 5.1 g 1,1-difluoroethane (containing 1,000 ppm VCM). The mixture was stirred and analyzed as containing 11.9 ppm VCM and the end of the experiment.

EXAMPLE 13

Example 11 was repeated using 99 weight percent sulfuric acid and a different glass frit. The average VCM concentration of the exit stream was 42 ppm and the average VFM concentration was 47 ppm.

EXAMPLE 14

A three liter flask is fitted with a 30 plate Oldershaw column. 199 ml of sulfuric acid were placed in the flask and continuously circulated to the top of the column at a rate of 74.7 ml/minute where it was allowed to drain back to the flask. A mixture of HFC-152a and 3.84 wt. % vinyl chloride was fed to the bottom of the column and removed at the top of the column at a rate of 11.7 g/hr. After about 2 hours, a sample of the HFC-152a mixture is determined to contain only about 0.7% of vinyl chloride monomer content. This example demonstrates a countercurrent flow contacting of sulfuric acid and a gas of HFC-152a and vinyl chloride.

EXAMPLE 15

A five liter flask is fitted with a 50 plate Oldershaw column. 264 ml of sulfuric acid were placed in the flask and continuously circulated to the top of the column at a rate of 74.7 ml/minute where it was allowed to drain back to the flask. A mixture of HFC-152a and 4.62 wt. % vinyl chloride was fed to the bottom of the column and removed at the top of the column at a rate of 11.7 g/hr. After about 3 hours, a sample of the HFC-152a mixture is determined to contain only about 0.4 wt. % of vinyl chloride monomer content. This example demonstrates a countercurrent flow contacting of sulfuric acid and a gas of HFC-152a and vinyl chloride.

What is claimed is:

1. A method of purifying 1,1-difluoroethane which comprises contacting a mixture comprising 1,1-difluoroethane and at least one unsaturated halocarbon having two carbon atoms with an effective amount of sulfuric acid under conditions sufficient to separate 1,1-difluoroethane from the at least one unsaturated halocarbon having two carbon atoms.

2. The method of claim 1 wherein the mixture comprises vinyl chloride.

3. The method of claim 1 wherein the mixture comprises vinyl fluoride.

4. The method of claim 1 wherein the mixture comprises a blend of vinyl fluoride and vinyl chloride.

5. The method of claim 1 wherein the amount of the at least one unsaturated halocarbon having two carbon atoms prior to the contacting ranges from about 0.1 ppm to about 10 weight percent based on the weight of the mixture.

6. The method of claim 1 wherein the separated 1,1-difluoroethane contains about 1 ppm or less of the at least one unsaturated halocarbon having two carbon atoms.

7. The method of claim 1 wherein the separated 1,1-difluoroethane contains about 0.1 ppm or less of the at least one unsaturated halocarbon having two carbon atoms.

8. A method of purifying 1,1-difluoroethane which comprises contacting a gaseous mixture comprising 1,1-difluoroethane and at least one unsaturated halocarbon having two carbon atoms with an effective amount of liquid sulfuric acid under conditions sufficient to separate 1,1-difluoroethane from the at least one unsaturated halocarbon having two carbon atoms.

9. The method of claim 8 wherein the mixture comprises vinyl chloride.

10. The method of claim 8 wherein the mixture comprises vinyl fluoride.

11. The method of claim 8 wherein the mixture comprises a blend of vinyl fluoride and vinyl chloride.

12. The method of claim 8 wherein the amount of the at least one unsaturated halocarbon having two carbon atoms prior to the contacting ranges from about 0.1 ppm to about 10 weight percent based on the weight of the mixture.

13. The method of claim 8 wherein the separated 1,1-difluoroethane contains about 1 ppm or less of at least one unsaturated halocarbon having two carbon atoms.

14. The method of claim 8 wherein the separated 1,1-difluoroethane contains about 0.1 ppm or less of at least one unsaturated halocarbon having two carbon atoms.

15. The method of claim 8 wherein the contacting is conducted in a vessel with agitation.

16. A method of purifying 1,1-difluoroethane which comprises contacting a gaseous mixture comprising 1,1-difluoroethane and at least one unsaturated halocarbon having two carbon atoms with liquid sulfuric acid by flowing the gaseous mixture through a vessel and flowing an effective amount of liquid sulfuric acid through the vessel countercurrent to the gaseous mixture to thereby separate 1,1-difluoroethane from the at least one unsaturated halocarbon having two carbon atoms.

17. The method of claim 16 wherein the mixture comprises vinyl chloride.

18. The method of claim 16 wherein the mixture comprises vinyl fluoride.

19. The method of claim 16 wherein the mixture comprises a blend of vinyl fluoride and vinyl chloride.

20. The method of claim 16 wherein the amount of the at least one unsaturated halocarbon having two carbon atoms prior to the contacting ranges from about 0.1 ppm to about 10 weight percent based on the weight of the mixture.

21. The method of claim 16 wherein the separated 1,1-difluoroethane contains about 1 ppm or less of the at least one unsaturated halocarbon having two carbon atoms.

22. The method of claim 16 wherein the separated 1,1-difluoroethane contains about 0.1 ppm or less of the at least one unsaturated halocarbon having two carbon atoms.

* * * * *